United States Patent [19]

Schricker et al.

[11] Patent Number: 4,904,473

[45] Date of Patent: Feb. 27, 1990

[54] RUMINANT FEED ANTACID CONTAINING POTASSIUM, SODIUM AND CHLORINE

[75] Inventors: Brian R. Schricker; Vikram P. Mehrotra, both of Terre Haute, Ind.

[73] Assignee: International Minerals & Chemical Corp., Northbrook, Ill.

[21] Appl. No.: 877,313

[22] Filed: Jun. 23, 1986

[51] Int. Cl.$^4$ .................. A23K 1/18; A61K 33/14; A61K 33/08

[52] U.S. Cl. ................................ 424/438; 424/601; 424/677; 424/679; 424/680; 424/692; 424/715

[58] Field of Search ..................... 424/153, 157, 438

[56] References Cited

U.S. PATENT DOCUMENTS

| | | | |
|---|---|---|---|
| 3,577,513 | 5/1971 | Roebuck et al. | 424/22 |
| 4,027,043 | 5/1977 | Schroeder et al. | 426/69 |
| 4,171,385 | 10/1979 | Skoch et al. | 426/658 |
| 4,171,386 | 10/1979 | Scoch et al. | 426/658 |
| 4,452,779 | 6/1984 | Cockerill | 424/128 |
| 4,540,577 | 9/1985 | Hunt et al. | 424/153 |

OTHER PUBLICATIONS

*Handbook of Nonprescription Drugs,* Fifth Edition, Published by Amer. Pharm. Assoc., p. 8.

Schneider et al., "Influence of Dietary Sodium and Potassium Bicarbonate and Total Potassium on Heat-Stressed Lactating Dairy Cows", *Journal of Dairy Science,* vol. 67, pp. 2546–2553 (1984).

*Primary Examiner*—Frederick E. Waddell
*Attorney, Agent, or Firm*—Wendell Ray Guffey; Thomas L. Farquer

[57] ABSTRACT

A pelletized feed supplement is supplied which effectively increases productivity of animals fed high acid producing diets. The pelletized feed supplement can also be used to neutralize stomach acid of humans and to maintain a proper electrolyte balance. A method is taught of producing the pelletized feed supplement which results in a buffering agent which is dissolved gradually, and has a high buffering capacity.

6 Claims, 2 Drawing Sheets

RUMINANT FEED ANTACID CONTAINING POTASSIUM, SODIUM AND CHLORINE

FIELD OF THE INVENTION

The present invention relates to a product which can be fed to lactating ruminants to buffer and neutralize the pH of the rumen and to provide potassium, chlorine, and sodium in the diet. The invention also relates to a product which may be used to neutralize acidity in an animal gut, including the avian or human gut.

BACKGROUND OF THE INVENTION

Current ruminant feeding practices rely heavily on readily fermentable carbohydrates and chopped, ensiled forages. Such feeds generate acid in the rumen which is not counterbalanced by dietary or endogenous bases and buffers. Under acidic conditions, the population of microorganisms found in the rumen are less desirable than those found under neutral or slightly basic conditions. Under neutral or slightly basic conditions, rumen microorganisms produce more fatty acids, which can be used by the lactating animal to produce milk fat.

It is known that sodium bicarbonate and magnesium oxide, alone or in combination, are effective in increasing the milk and/or milk fat production of animals fed on high acid-producing diets. Chalupa and Kronfeld, 1983, Animal Nutrition and Health, May–June, 50; Erdman, et al. 1982, Journal of Dairy Science, 65, 712; Erdman, et al. 1980, Journal of Dairy Science, 63, 923; and Kilmer et al. 1980, Journal of Dairy Science, 63, 2026. However, these additives have the undesirable effects of temporarily reducing the feed intake and decreasing the serum levels of potassium and magnesium.

SUMMARY OF THE INVENTION

It is an object of the present invention to provide a feed supplement to improve the yield of milk fat produced by ruminants.

It is a further object of the invention to provide a feed supplement which serves to neutralize acids produced in the rumen or gut of animals, including avians and humans.

It is yet another object of the present invention to provide electrolytes and antacids in a form such that the active ingredients are released gradually over time.

It is still another object of the invention to provide a sodium or magnesium antacid balanced with respect to potassium, sodium and chlorine to maintain the electrolyte balance under heat stress conditions.

It is yet another object of the present invention to provide a pelletized feed supplement in a form which is resistant to abrasion.

Other objects of the invention will be apparent to those skilled in the art from the following detailed description and claims.

The foregoing objects of the present invention are achieved by providing a pellet comprising an antacid selected from the group consisting of sodium and magnesium antacids, said pellet containing potassium, sodium and chlorine in a weight ratio of from about 1.5 to about 1.8 parts of potassium and from about 1.2 to about 1.5 parts of chlorine per part of sodium, said potassium being present in sufficient amount to provide from about 0.8 to about 1 weight parts of potassium per weight part of any magnesium present. Methods of producing the pelletized feed supplement and of administering said feed supplement to both ruminants and humans are also contemplated by this invention.

The pelletized feed supplement of the invention provides several advantages over currently available buffers such as sodium bicarbonate and trona. The pelletized feed provides a nutritionally balanced mixture of the essential elements for maintaining electrolyte balance of potassium, magnesium, chlorine, and sodium. The pelletized feed supplement produces a more gradual change in the pH of the rumen than known bicarbonate buffers. Also, the pelletized feed supplement has a higher buffering capacity than sodium bicarbonate on a weight for weight basis. At higher pH's, the population of microorganisms in the rumen produces more fatty acids which may be used in milk production.

DETAILED DESCRIPTION OF THE INVENTION

Figure 1:
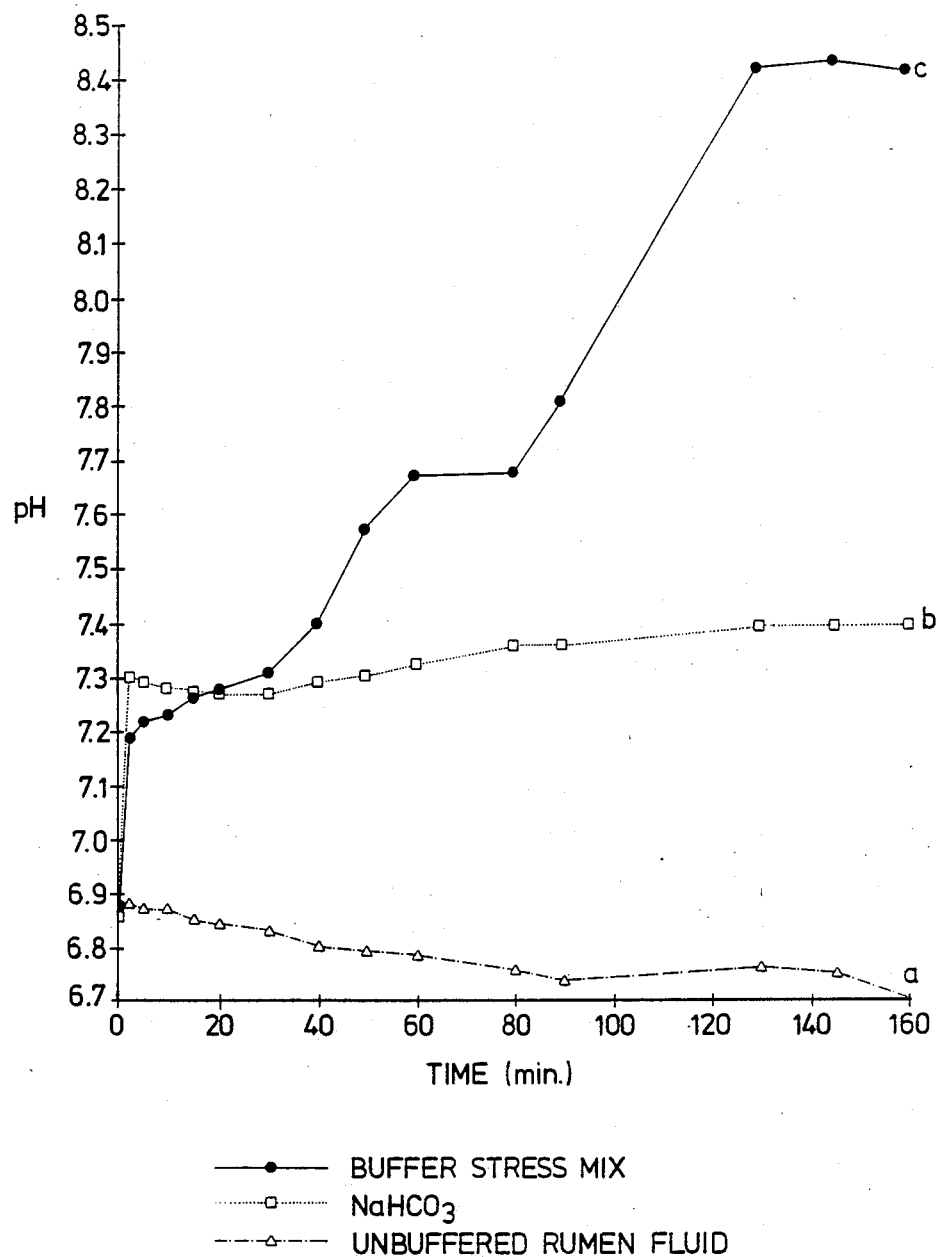
FIG. 1 shows the change in pH over time of strained rumen fluid in an anaerobic chamber. Curve (a) shows the change in unbuffered rumen fluid. Curve (b) shows the pH change in bicarbonate buffered rumen fluid. Curve (c) shows the pH change in rumen fluid treated with the pelletized feed supplement of the present invention.

The antacid and electrolyte sources which are used to make the pellets of the present invention can be any feed grade or better quality material which is not toxic to the animal. The antacids which may be used include magnesium oxide, sodium bicarbonate, dolomite, sodium hydroxide, calcium hydroxide, calcium carbonate, magnesium carbonate, sodium carbonate, northupite and mixtures thereof. Suitable electrolyte sources which may be used in the practice of the invention are any that are conventionally used as animal or human nutritional supplements, including potassium chloride, langbeinite, potassium bicarbonate, arcanite, potassium hydroxide, potassium phosphates, potassium carbonate, sodium chloride, and mixtures thereof. It is important that the weight ratio among elements be within about 10% of 1.65:1:1.35:1.88 of K:Na:Cl:Mg, that is to say the pellet should contain from about 1.5 to about 1.8 parts of potassium and from about 1.2 to about 1.5 parts of chlorine per part of sodium. The magnesium is not required, but if it is supplied in the antacid, it should be balanced by the other elements in the appropriate ratio. That is to say that magnesium: potassium should be within about 10% of 1.14:1, or from about 0.8 to about 1 weight parts of potassium per weight part of any magnesium present. The amounts and types of electrolytes to be added to the antacid to provide the specified ratios can be readily chosen by one skilled in the art.

In the preferred embodiment of the invention, the components of the pellets are agglomerated to form pellets having a size of at least about plus 48 mesh and desirably from about 48 to about 8 Tyler mesh. It has been determined that the rate at which the pellets dissolve in the rumen or stomach is greatly decreased if the components, of the pellet, e.g., the antacid and electrolytes, are ground prior to agglomeration. Generally, the particle size of the components should be reduced to less than 100 Tyler mesh, and preferably to less than 250 mesh.

Surprisingly, it has been found in accordance with this invention that agglomeration not only slows the rate of dissolution of the pelletized feed supplement, but also causes a greater total pH change in the rumen or stomach than unagglomerated material. Reasons for the alteration in the antacid characteristics of the pelletized feed supplement are not precisely known. However, it has been found that the preferred method of preparing the pellets of the present invention, i.e. grinding of the ingredients to achieve a substantially uniform particle size of less than 100 Tyler mesh and agglomerating, results in a chemical reaction.

Generally, there is a range of about 5% by weight of the dry ingredients of liquid which may be employed for any particular composition which will achieve pellets of appropriate sizes and durability. This range will vary with the particular materials employed in the composition and the size of the materials. The range for a particular composition can be determined by routine testing. Too much liquid will lead to pellets which are too large and which are wet and sticky. Too little water will lead to particles which are too small, and are additionally weak and crumbly. Generally, as the fineness of the particles increases, more liquid is required to agglomerate properly. Liquids other than water may be used, for example, a solution of choline chloride may be used advantageously. Amounts of water or other liquid which are added to form pellets are generally between about 10 and 25% by weight of the other ingredients. This proportion of liquid to solids produces pellets of appropriate dimensions.

It also has been found that when binders, such as starch, hydraulic cement, and clay binders, are added to the pelletized feed supplement, the resistance of the pellets to breakage and abrasion is increased. In one preferred embodiment bentonite (a clay binder) is added to the formulation for the pelletized feed supplement. Suitable amounts of bentonite are generally less than about 5% by weight, and preferably about 2%. Further, it has been found that addition of certain widely used components such as molasses may have an adverse effect on the dissolution characteristics of the pelletized feed supplement, causing the solubilization rate to increase. Conversely components such as cement and bentonite decrease the rate of solubilization.

The initial ingredients may be ground individually or together to achieve good mixing. This may be accomplished by any of the means known in the art, such as using ball mills, jet mills, pulverizers and hammer mills. Any means which will achieve the desired degree of fineness is suitable. The inventors have found that a disc pelletizer is well-suited for carrying out the agglomeration of the ground materials, although other apparati may be used. The agglomeration of the ground ingredients may be performed by drum, disc, cone or pan pelletizers, pressure compaction, extrusion, or any other means known in the art.

After the pellets have been formed by agglomeration, they may be dried at either ambient or higher temperatures to remove moisture. A vibrating fluidized bed dryer has been found to be suitable for this purpose. The dried particles can be screened to ensure that they are of the proper dimensions. Oversized granules may be discarded or reduced in size, for example, by means of a knife granulator.

After the processing involved in producing the pellets of the present invention, new compounds may be found, indicating that a chemical reaction has occurred. For example, when potassium chloride, langbeinite, magnesium oxide and sodium bicarbonate are present in the initial mixture, northupite has been detected by means of x-ray diffraction in the pelletized product as a major reaction product. Thus, the method of the present invention provides a means of making northupite. Arcanite has also been tentatively identified in the product.

The pelletized feed supplement may conveniently be admixed with an animal feed. Suitable amounts of the pelletized feed supplement to be admixed with the feed are between 0.5 and 5% by weight of the feed. Preferred amounts are between 2 and 4%.

It is also contemplated that the pelletized product of the present invention may be used by humans. The pelletized feed supplement could be admixed with food, or preferably could be swallowed as a tablet. Such administration would have the beneficial effects of reducing the acidity of the stomach (alleviating heartburn) and helping to maintain the electrolyte balance, which is often perturned under heat stress conditions, such as after strenuous exercise. Suitable amounts of the pelletized feed supplement to be administered to humans are between about 0.3 and about 0.8 grams per kilogram of body weight.

The following examples are not intended to limit the invention but merely exemplify particular embodiments thereof.

EXAMPLE 1

An in situ method was used to evaluate the relative rate of dissolution of selected agglomerated pelletized feed supplement formulations compared to sodium bicarbonate.

A 5 g sample of the test material was placed in a labelled, dry, nylon bag. The bags were secured to an iron weight and placed into the ventral section of the rumen of a fistulated steer. After a given period of time the bags were removed, rinsed with deionized water to remove attached external particles, and then dried overnight at 100° C. After equilibrating to room temperature the bags were reweighed. The percent disappearance was determined from the test material weight loss. The data are shown below.

TABLE 1

| | Duration of Rumen Exposure (hrs) | Material Loss (g) | Material Loss (%) |
|---|---|---|---|
| Pelletized feed supplement | 8 | 1.38 | 27.6 |
| NaHCO$_3$ | 8 | 4.35 | 87.0 |
| Pelletized feed supplement | 16 | 1.52 | 30.4 |
| NaHCO$_3$ | 16 | 4.97 | 99.4 |
| Pelletized feed supplement | 24 | 2.43 | 48.6 |
| NaHCO$_3$ | 24 | 4.91 | 98.2 |

The composition of the pelletized feed supplement tested in these examples consisted of 26.15% MgO, 32.65% NaHCO$_3$, 22.85% KCl, 16.35% langbeinite, 2.5% sodium-bentonite, 12.5 weight % deionized water. All the dry ingredients were ground to a particle size of less than 250 mesh prior to agglomeration.

These data indicate that the pelletized feed supplement dissolved more slowly in the rumen than sodium bicarbonate.

EXAMPLE 2

The in situ method described above was used to compare agglomerated with unagglomerated formulations.

The data shown below in Table 3 demonstrate that agglomeration reduces the amount of dissolution in 24 hours. The compositions used are described in Table 2.

TABLE 2

Description of Rumen Buffer Stress Mix Formulations

| Rumen Buffer Stress Mix No. | Ingredients (%) | | | | | |
| --- | --- | --- | --- | --- | --- | --- |
| | MgO | NaHCO$_3$ | KCl | Langbeinite | Choline Chloride 70% Soln. | Deionized Water |
| 1 | 26.48 | 32.41 | 23.52 | 17.59 | 12.0 | 10 |
| 2 | 26.23 | 32.09 | 23.28 | 17.41 | 12.0 | 11 |

All ingredients were ground for 30 minutes before agglomeration. The liquid components are omitted from the % calculation of dry ingredients.

TABLE 3

In Situ Evaluation of Buffer/Stress Mix Formulations: Agglomerated vs. Unagglomerated

| Material Description and No. | Duration of Rumen Exposure (h) | Material Loss (g) | Material Loss (%) |
| --- | --- | --- | --- |
| #1, agglomerated | 24 | 2.781 | 55.62 |
| #1, unagglomerated | 24 | 2.942 | 58.84 |
| #2, agglomerated | 24 | 2.856 | 57.12 |
| #2, unagglomerated | 24 | 2.936 | 58.72 |

EXAMPLE 3

An in vitro method of evaluating the pelletized feed supplement was used with strained rumen fluid in an anaerobic chamber. For each sample to be tested, three 200 ml Erlenmeyer flasks were used: one for the pelletized feed supplement (composition as described in Example 1), one for the sodium bicarbonate control, and one for the unbuffered rumen fluid. Comparisons were made on a gram-equivalent sodium bicarbonate basis. Equal quantities of rumen fluid were added to the flasks containing their respective treatments. All flasks were stirred on magnetic stir plates at a constant rate. Measurement of the pH of the contents of the flasks were made at various times. As can been seen in FIG. 1, the pelletized feed supplement caused a more gradual change in the rumen pH than did the sodium bicarbonate. In addition the absolute magnitude of the change was much greater, the pelletized feed supplement achieving a pH of approximately 8.4 within 2 hours, while the bicarbonate buffered sample only reached a pH of 7.3.

EXAMPLE 4

The in vitro method described in Example 3 was used to compare agglomerated versus unagglomerated buffer stress mix. The composition of the buffer stress mix was: 23.72% MgO, 29.64% NaHCO$_3$, 20.75% KCl 14.82% langbeinite, 11.07% dry choline chloride (60%), 20% deionized water. The dry ingredients were ground to a particle size of less than 250 mesh prior to agglomeration.

Figure 2:
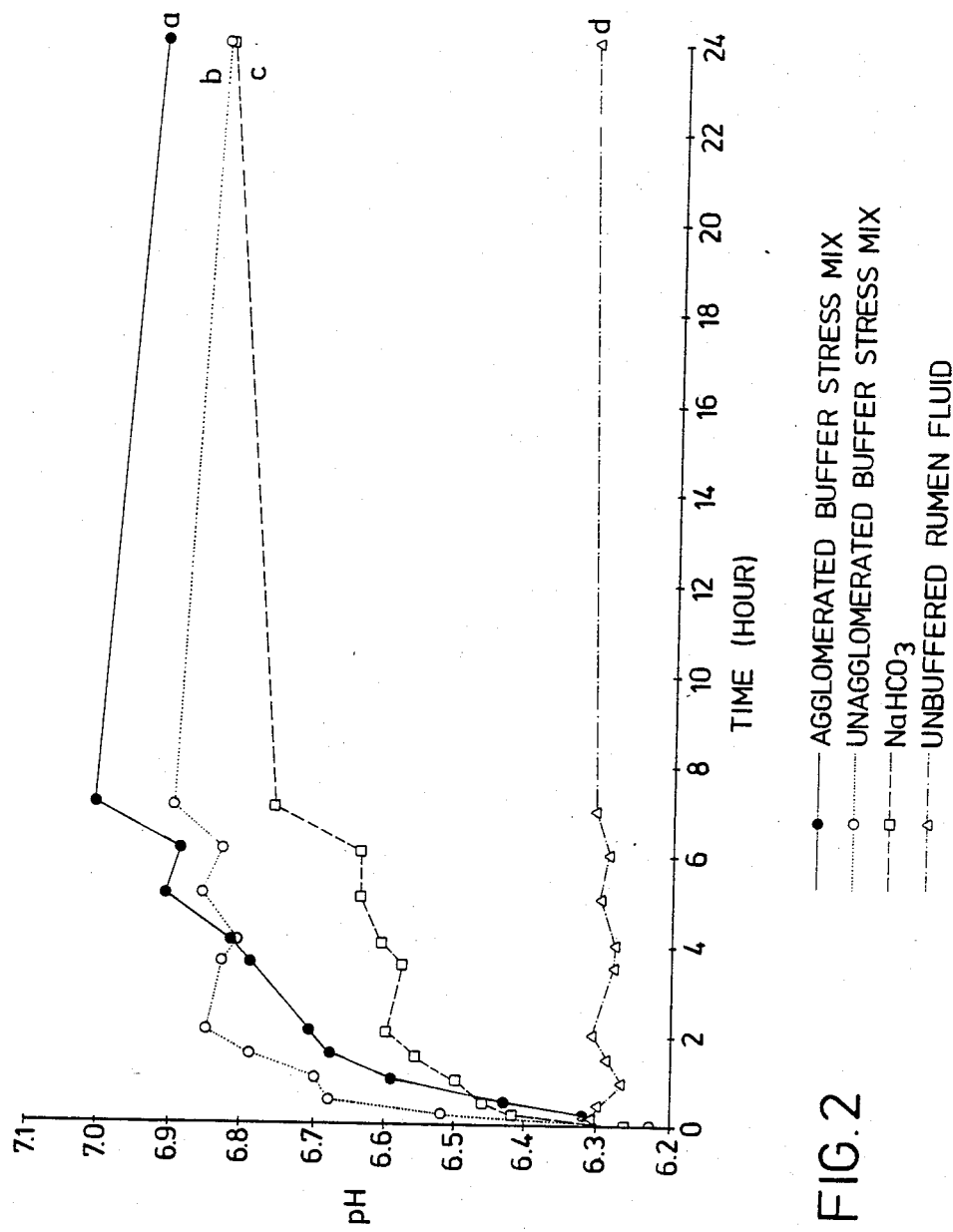
FIG. 2 shows the difference in rate of dissolution of agglomerated (curve a) versus unagglomerated (curve b) rumen buffer.

As shown in FIG. 2, the agglomerated formulation dissolved more slowly than the unagglomerated, and caused a greater pH change.

EXAMPLE 5

Four groups of three cows each were fed on four different regimes in a Latin square design. One treatment was 1% sodium bicarbonate supplemented feed. Another treatment was 1% of the pelletized feed supplement described in Example 1 in the feed. A third treatment was 3% of the pelletized feed supplement described in Example 1 in the feed. The control treatment was unsupplemented feed. The feed which all groups received was a highly fermentable and acid generating ration. The ration contained 30% coarsely-ground wheat, 15% soybean meal, 10% ground corn, 40% corn silage, and 5% coastal bermuda grass hay. The cows were fed two times daily and milked two times daily. The test period ran for 28 days. Milk samples were taken on days 20, 21, 27 and 28 of each period to analyze for composition.

As can be seen in the results shown below in Table 4, dry matter intake was not effected significantly by any of the treatments relative to the control. In addition, milk yield was not substantially effected by any of the treatments. However, the yield of milk fat was substantially effected by the buffer treatments, with the 3% pelletized feed supplement causing the greatest yield improvement. The 1% NaHCO$_3$ and 1% pelletized feed supplement regime improved the 4% fat corrected milk by about 5%, while the 3% pelletized feed supplement regime enhanced this parameter by about 11%. These data indicate that the pelletized feed supplement of the present invention is as effective or more effective than NaHCO$_3$ as an alkalizing agent or buffer for dairy rations. The 3% pelletized feed supplement contains equivalent quantities of NaHCO$_3$ as 1% NaHCO$_3$, and yet it enhanced performance to a greater extent.

TABLE 4

| | Control | 1% NaHCO$_3$ | 1% Pelletized Supplement | 3% Pelletized Supplement |
| --- | --- | --- | --- | --- |
| Dry Matter Intake, (kg/cow/day) | 17.4 | 17.7 | 17.4 | 17.4 |
| Milk Yield, (kg/cow/day) | 18.9 | 19.1 | 18.4 | 18.7 |
| Milk Fat, (%) | 2.97 | 3.21 | 3.43 | 3.67 |
| Milk Fat Yield, (kg/cow/day) | 0.59 | 0.60 | 0.61 | 0.67 |
| 4% fat corrected milk (kg/cow/day) | 15.8 | 16.7 | 16.5 | 17.5 |

We claim:

1. A method of producing a pellet suitable for use as a pelletized feed supplement, comprising:
forming a mixture of an antacid selected from the group consisting of sodium and magnesium antacids and an electrolyte selected from the group consisting of potassium, sodium, and chlorine containing electrolytes, said electrolyte and said antacid having a particle size of less than 100 Tyler mesh, said electrolyte supplying said pellet with sufficient potassium, sodium and chlorine so that the weight ratio in said pellet is from about 1.5 to about 1.8 parts potassium and from about 1.2 to about 1.5 parts chlorine per part sodium, and sufficient potassium to provide about 0.8 to about 1 weight parts of potassium per weight part of any magnesium present; and agglomerating said mixture to form particles having an average particle size of between about 48 and 8 Tyler mesh.

2. The method of claim 1 further comprising forming said mixture with a binder.

3. The method of claim 2 wherein said binder is bentonite, said bentonite comprising less than about 5% by weight of said mixture.

4. The method of claim 1 wherein said pellet has been formed by agglomeration of components having a particle size of less than about 250 Tyler mesh.

5. The method of claim 1 wherein said electrolyte is selected from the group cosisting of potassium chloride, langbeinite, potassium bicarbonate, arcanite, potassium hydroxide, potassium phosphates, potassium carbonate, sodium chloride, and mixtures thereof.

6. The method of claim 1 wherein said antacid is selected from the group consisting of magnesium oxide, sodium bicarbonate, northupite, and mixtures thereof.

* * * * *

UNITED STATES PATENT AND TRADEMARK OFFICE
CERTIFICATE OF CORRECTION

PATENT NO. : 4,904,473
DATED : February 27, 1990
INVENTOR(S) : Brian R. Schricker and Vikram P. Mehrotra It is certified that error appears in the above-identified patent and that said Letters Patent is hereby corrected as shown below:

Column 1, line 34, "effets" should read --effects--
Column 4, line 21, "pertuned" should read --perturbed--
Column 8, line 8, Claim 5, "cosisting" should read --consisting--

Signed and Sealed this

Fourth Day of December, 1990

Attest:

HARRY F. MANBECK, JR.

*Attesting Officer*     *Commissioner of Patents and Trademarks*